United States Patent [19]

Kissel

[11] Patent Number: 5,279,940

[45] Date of Patent: Jan. 18, 1994

[54] CHEMILUMINESCENT COMPOSITION CONTAINING CATIONIC SURFACTANTS OR POLYMERS AND 4'-HYDROXYACETANILIDE, TEST KITS AND THEIR USE IN ANALYTICAL METHODS

[75] Inventor: Thomas R. Kissel, Rochester, N.Y.

[73] Assignee: Eastman Kodak Company, Rochester, N.Y.

[21] Appl. No.: 923,662

[22] Filed: Aug. 3, 1992

[51] Int. Cl.$^5$ .................... C12Q 1/68; C12Q 1/28; G01N 33/535; C09K 11/00
[52] U.S. Cl. ........................ 435/6; 252/700; 435/7.9; 435/7.91; 435/7.92; 435/28; 435/810; 435/968; 436/172; 436/518
[58] Field of Search ............ 252/700, 186, 29; 436/164, 543, 826, 172; 435/4, 5, 6, 7.2, 7.95, 968, 7.79, 7.791, 810

[56] References Cited

U.S. PATENT DOCUMENTS

| | | | |
|---|---|---|---|
| 4,450,305 | 5/1984 | Kamhi | 568/611 |
| 4,462,931 | 7/1984 | Cohen | 252/700 |
| 4,521,511 | 6/1985 | Stout | 435/28 |
| 4,598,044 | 7/1986 | Kricka et al. | 435/28 |
| 4,729,950 | 3/1988 | Kricks | 435/28 |
| 4,828,983 | 5/1989 | McClune | 435/7 |
| 4,859,369 | 8/1989 | Baretz et al. | 252/700 |
| 4,891,324 | 1/1990 | Pease et al. | 436/519 |
| 4,927,769 | 5/1990 | Chang | 436/518 |
| 4,959,182 | 9/1990 | Shaap | 252/700 |
| 5,004,565 | 4/1991 | Shaap | 252/700 |
| 5,093,270 | 3/1992 | Chang | 436/518 |
| 5,106,732 | 4/1992 | Kondo et al. | 435/28 |

FOREIGN PATENT DOCUMENTS

| | | |
|---|---|---|
| 201713 | 8/1982 | Czechoslovakia . |
| 116454 | 8/1984 | European Pat. Off. . |
| 473984 | 3/1992 | European Pat. Off. . |
| 3921609 | 6/1989 | Fed. Rep. of Germany . |
| 82/01713 | 11/1983 | Netherlands . |

OTHER PUBLICATIONS

Abdel-Latif et al., (Analytica Chemica Acta (1989) 221: 11–17.
Diamantis, E. Clin Biochem (1990) 23:437–443.
Chemical Abstracts, vol. 114, 8567h, p. 99 (1991).
Gorovits et al, *Doklady Akademii Nauk SSR*, vol. 307(4), pp. 1004–1006 (1989).
Hoshino et al, *Analytical Chemistry*, vol. 59, pp. 496–504 (1987).
Das et al., *Colloids and Surfaces*, vol. 35, pp. 101–104 (1989).
Igarashi et al, *Analytical Chemistry*, vol. 60, pp. 446–450 (1988).
Malehorn et al, *Analyst*, vol. III, pp. 941–947 (1986).
Karatani, *Bull., Chemical Society of Japan*, vol. 60, pp. 2023–2029 (1987).
Lasovsky et al., *Bioelectrochemistry and Bioenergetics*, vol. 15, pp. 95–102 (1986).
Sakaiguchi et al, *Bull. Chemical Society of Japan*, vol. 61, pp. 2743–2746 (1988).
Hinze, *Contri. Cient. Tecnol.*, Numero Espec., pp. 20–23 (1985).
Kricka et al., *Pure & Appl. Chem.*, vol. 59(5), pp. 651–654 (1987).
Ohshima et al, *Analytica Chimica Acta*, vol. 232, Pp. 385–388 (1990).
Thorpe et al, *Clinical Chemistry*, vol. 31(8), pp. 1335–1341 (1985).
Kricka et al, *Archives of Biochemistry and Biophysics*, vol. 217 (2), pp. 674–681 (1982).

*Primary Examiner*—Margaret Parr
*Assistant Examiner*—Carla Myers
*Attorney, Agent, or Firm*—J. Lanny Tucker

[57] ABSTRACT

An aqueous composition useful for providing a chemiluminescent signal in analytical methods is stabilized by the presence of specific amounts of either a low molecular weight cationic surfactant or a cationic polymer. The composition also includes a 2,3-dihydro-1,4-phthalazinedione derivative, such as luminol, and 4'-hydroxyacetanilide. A chemluminescent signal is generated using the composition in the presence of peroxidase or a peroxidase-labeled specific binding species (such as an antibody or oligonucleotide).

23 Claims, No Drawings

CHEMILUMINESCENT COMPOSITION CONTAINING CATIONIC SURFACTANTS OR POLYMERS AND 4'-HYDROXYACETANILIDE, TEST KITS AND THEIR USE IN ANALYTICAL METHODS

FIELD OF THE INVENTION

This invention relates to the field of analytical and diagnostic chemistry for the detection of various analytes in biological fluids. In particular, it relates to a signal-generating composition useful in chemiluminescent assays, to test kits containing same and analytical methods in which the composition and test kits can be used.

BACKGROUND OF THE INVENTION

Luminescent and luminometric assays are those which produce an emission of light as a result of the presence of an analyte of interest. The light emission is generally of sufficient duration for it to be measured or detected and thereby allow the determination of the analyte.

There are several major types of assays whereby a chemiluminescent signal can be used to advantage to determine an analyte:

1) Assays where a chemiluminescent compound is used to directly label a specific binding ligand such as proteins, oligonucleotides, antigens, haptens, hormones, nucleic acids and other compounds of biological interest. Chemiluminescence can be detected by adding a peroxidase and an oxidant to the labeled ligand.

2) Assays where catalysts or cofactors of luminescent reactions are used as labels for specific binding ligands. For example, peroxidase can be conjugated to ligands and used to provide a chemiluminescent signal.

3) Assays where chemiluminescent reactions are used to determine the products formed by action of an enzyme label other than peroxidase on suitable substrates. An example of this type of assay is the determination of a glucose oxidase-labeled specific binding ligand by generating hydrogen peroxide in the presence of peroxidase.

4) Non-immunoassays to determine a peroxidase or oxidant such as hydrogen peroxide generated as a result of a non-immunoreactant analyte.

Further details of such assays are provided in extensive literature such as U.S. Pat. No. 4,729,950 (Kricka et al) and publications noted therein.

A common reaction system used to generate chemiluminescent signals is that utilizing a 2,3-dihydro-1,4-phthalazinedione derivative (identified herein as a "DPD"), such as luminol or isoluminol, as a substrate for peroxidative action. Attempts have been made to improve the sensitivity of chemiluminescent assays, including those where a DPD is used. For example, U.S. Pat. No. 4,729,950 (noted above) describes the use of certain aromatic amine enhancers. Similarly, certain aromatic phenols are described for the same purpose in U.S. Pat. No. 4,598,044 (Kricka et al).

This technology has been used commercially to some success, but there is a need for further improvement in sensitivity at very low analyte concentration, increased storage stability of reagents and kinetic stability (that is, duration of constant light output).

The use of micelles to improve chemiluminescence with various systems is described in considerable literature, including U.S. Pat. No. 4,462,931 (Cohen et al), U.S. Pat. No. 4,927,769 (Chang et al) and U.S. Pat. No. 4,959,182 (Schaap) and by Hinze, *Contri. Cient. Tecnol.* 1985, Numero Espec., pp. 20–23.

It would seem apparent that micelles could be combined with enhancers to obtain even further improvements in chemiluminescence, but it has been observed that such is not true when the enhancers of U.S. Pat. No. 4,598,044 (such as p-iodophenol) are used with micelles.

SUMMARY OF THE INVENTION

The problems noted with known chemiluminescent systems described above are overcome with an aqueous composition for providing a chemiluminescent signal having a pH of from about 7 to about 9.5 and comprising:

a) a 2,3-dihydro-1,4-phthalazinedione derivative,
b) a low molecular weight cationic surfactant present at from about 0.05 to about 0.25% above its critical micelle concentration, or from about 0.01 to about 2% of a cationic polymer, and
c) 4'-hydroxyacetanilide.

This invention also provides a diagnostic test kit comprising, individually packaged:

a) a 2,3-dihydro-1,4-phthalazinedione derivative, and one or more of the following reagents:
  b) a low molecular weight cationic surfactant present at from about 0.05 to about 0.25% above its critical micelle concentration, or from about 0.01 to about 2% of a cationic polymer,
  c) 4'-hydroxyacetanilide, and
  d) a peroxidase or peroxidase-labeled specific binding species.

Moreover, a method for producing a chemiluminescent signal in response to a peroxidase comprises:

A. reacting a peroxidase in the presence of:
  a 2,3-dihydro-1,4-phthalazinedione derivative,
  an oxidant,
  a low molecular weight cationic surfactant present at from about 0.05 to about 0.25% above its critical micelle concentration, or from about 0.01 to about 2% of a cationic polymer, and
  4'-hydroxyacetanilide to produce a chemiluminescent signal, and B. determining the resulting signal as a measure of the peroxidase.

A specific binding assay for the determination of a specific binding ligand comprises:

A. complexing a specific binding ligand with a receptor specific for the ligand to form a specific binding complex, B. labeling the specific binding complex with a peroxidase which is either conjugated with the receptor, or is conjugated with a specific binding molecule which is specifically reactive with either the specific binding ligand or the receptor, C. after separating uncomplexed materials from the peroxidase-labeled complex, contacting the peroxidase-labeled complex with:
  a 2,3-dihydro-1,4-phthalazinedione derivative,
  an oxidant,
  a low molecular weight cationic surfactant present at from about 0.05 to about 0.25% above its critical micelle concentration, or from about 0.01 to about 2% of a cationic polymer, and
  4'-hydroxyacetanilide to produce a chemiluminescent signal, and B. determining the resulting signal as a measure of the specific binding ligand.

The present invention provides all of the known advantages associated with the use of chemiluminescent detection in analytical, immunochemical and hybridization assays. However, additional unexpected advantages have been achieved, namely better kinetic stability, higher sensitivity at low analyte concentrations and more linear calibration curves. By "kinetic stability" is meant increased duration of constant light output These results are achieved by using 4'-hydroxyacetanilide as a chemiluminescent enhancer in cationic micelles formed from low molecular weight cationic surfactants or cationic hydrophilic polymers. Other known enhancers did not provide such advantages, even in the presence of cationic micelles.

DETAILED DESCRIPTION OF THE INVENTION

The present invention can be practiced to advantage in any analytical method designed to generate a chemiluminescent signal in response to the presence of a peroxidase and a 2,3-dihydro-1,4-phthalazinedione derivative (identified herein as "DPD"). Such assays can involve the detection of hydrogen peroxide or peroxidase (in its free form) for the detection of a non-immunological analyte other than peroxidase or hydrogen peroxide. In particular, the invention is useful in the practice of specific binding assays which generate a chemiluminescent signal, such as those assays (but not limited to) described above in the Background of the Invention. The remainder of this discussion will be directed to specific binding assays as particularly descriptive of the present invention.

The improved aqueous composition of this invention includes 4'-hydroxyacetanilide as a chemiluminescence enhancer to increase the signal over that obtained in its absence Moreover, any free or conjugated 2,3-dihydro-1,4-phthalazinedione derivative that can be converted to an excited state in a chemiluminescent reaction and then returns to a non-excited state with the emission of light, is useful in the practice of this invention. A considerable number of such compounds are known in the art, including those described in U.S. Pat. No. 4,598,044 and *Chemiluminescence in Organic Chemistry*, Gundermann and McCapra Springer-Verlag, Berlin, 1987, pages 204-207. Such compounds are generally known as "luminol type hydrazides" and include phthalic hydrazides, naphthalene-1,2-dicarboxlyic acid hydrazides, anthracene-2,3-dicarboxylic hydrazides, phenathrenedicarboxylic hydrazides, fluorene-1,2-dicarboxylic acid hydrazides, benzo[g,h,i]perylene-1,2-dicarboxylic hydrazides, coronene-1,2-dicarboxylic acid hydrazides, and others readily apparent to one skilled in the art.

In particular, the DPD is defined by the structure (II):

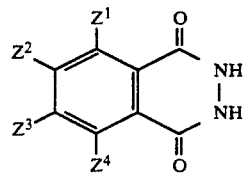

wherein $Z^1$, $Z^2$, $Z^3$ and $Z^4$ are independently hydrogen, alkyl of 1 to 6 carbon atoms (such as methyl, ethyl, isopropyl, t-butyl, sec-pentyl and hexyl), alkenyl of 2 to 6 carbon atoms [such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl], hydroxy, alkoxy of 1 to 6 carbon atoms (such as methoxy, ethoxy, isopropoxy, t-butoxy and hexoxy), carboxy, amino [including amino substituted with alkyl or alkanoyl, such as methylamino, ethylamino, amido (for example, acetamido and hexanamido), dimethylamino, diethylamino and diisobutylamino], conjugated aminoalkenyl (for example, as defined below) or aminoaryl [including substituted aminoaryl, such as p-(N,N-dimethylamino)phenyl, p-(N,N-diethylamino)phenyl and 5-amino-2,3-dihydro-1,4-phthalazinedion-8-yl (also known as luminyl)].

At least one of $Z^1$ and $Z^2$ is amino (including substituted amino, as defined above), conjugated aminoalkenyl (including substituted aminoalkenyl as described above) or aminoaryl [such as p-(N,N-dimethylamino)phenyl, p-(N,N-diethylamino)phenyl and 5-amino-2,3-dihydro-1,4-phthalazinedion-8-yl]. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group [such as 2-(N,N-diisopropylamino)vinyl, 2-(N,N-diisobutylamino)vinyl and 2-(N,N-diisopentylamino)vinyl], and dialkylaminobutadienyl groups, such as 4-(N,N-diethylamino)-1,3-butadien-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or alkoxy of 1 to 4 carbon atoms (such as methoxy, ethoxy and isopropoxy). Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol (5-amino-2,3-dihydro-1,4-phthalazinedione) and isoluminol (6-amino-2,3-dihydro-1,4-phthalazinedione) are preferred, and luminol is most preferred.

Other useful classes of DPD compounds are described in the Gundermann and McCapra publication noted above, and include substituted or unsubstituted phthalic hydrazides, 4-substituted phthalhydrazides, anthracene-2,3-dicarboxylic hydrazides, phenathrene dicarboxylic hydrazides, fluorene-1,2-dicarboxylic acid hydrazides, benzo[g,h,i]perylene-1,2-dicarboxylic hydrazides and coronene-1,2-dicarboxylic acid hydrazides, such as those illustrated by the following structures:

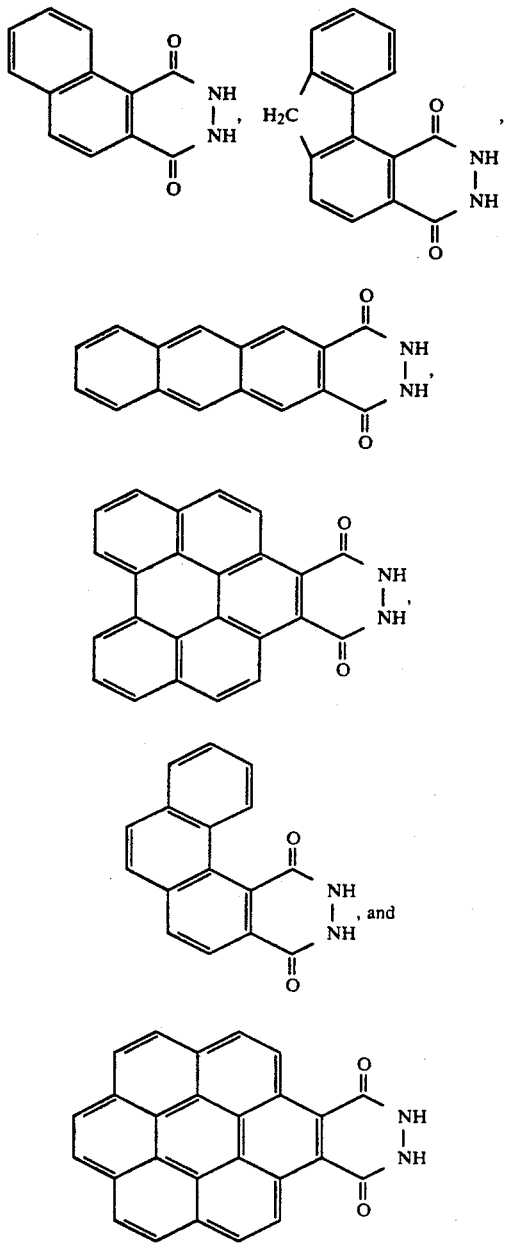

The present invention critically makes use of a low molecular weight cationic surfactant to provide micelles, or a cationic polymer to provide a hydrophobic environment for increased sensitivity, storage stability and kinetic stability.

Surfactants are compounds which lower the surface tension of water, as is well understood by one skilled in the art. Generally, such materials are synthetic, but some are naturally occurring. Cationic surfactants have a net positive charge and are described in a number of publications including, for example, *Surfactants and Interfacial Phenomena*, By Milton J. Rosen, John Wiley and Sons, N.Y., 1978, pages 13-17 and are identified by tradenames in *McCutcheon's Emulsifiers and Detergents*, North American Ed., MuCutcheon's Division, The Manufacturing Confectioner Publishing Co., 1988, page 259. Positive charges in the surfactants can be provided by cationic groups including, but not limited to, quaternary ammonium, quaternary phosphonium, sulfonium, pyridinium, pyrimidinium, imidazolium and oxonium.

Particularly useful cationic surfactants and polymers can be represented by the structure (I):

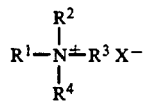

wherein $R^1$ is substituted or unsubstituted alkyl of at least 7 carbon atoms, and preferably from 10 to 20 carbon atoms (such as n-octyl, isononyl, isodecyl, dodecyl, tetradecyl, hexadecyl, octadecyl, eicosyl, 2,7,8-trimethyldecyl, 4-ethyl-6-methyldodecyl, benzyl and phenethyl), substituted or unsubstituted aryl of 6 to 14 carbon atoms in the aromatic nucleus (such as phenyl, naphthyl or anthryl) which can be substituted with one or more hydrophobic groups such as linear or branched alkyl of 1 to 10 carbon atoms (such as methyl, ethyl, isopropyl, t-butyl or hexyl), halo and others known to one skilled in the art. Such substituted aryl groups include, but are not limited to xylyl, tolyl, isononylphenyl, dimethylphenyl and trichlorophenyl. $R^1$ can also be substituted or unsubstituted alkenyl of 8 to 20 carbon atoms (such as 1-octenyl, 1-decenyl and 2-dodecenyl), or a polymeric moiety (described below).

Preferably, $R^1$ is alkyl or alkenyl of 14 to 16 carbon atoms, with groups such as 2,4-dimethyl-6-ethyldecyl, tetradecyl and hexadecyl being more preferred.

In structure (I), $R^2$ can be alkyl or alkenyl as defined for $R^1$, substituted or unsubstituted alkyl of 1 to 7 carbon atoms (such as methyl, ethyl, isopropyl, t-butyl, methoxymethyl, benzyl and hexyl), substituted or unsubstituted alkenyl of 2 to 7 carbon atoms (such as a ethenyl, allyl, isopropenyl and n-butenyl), or carbocyclic aryl of 6 to 10 carbon atoms in the ring system (such as phenyl, tolyl, xylyl, naphthyl and p-methoxyphenyl). One of $R^2$, $R^3$ and $R^4$ can be one of the nonpolymeric groups defined above for $R^1$.

$R^3$ and $R^4$ are independently substituted or unsubstituted alkyl of 1 to 7 carbon atoms (such as methyl, ethyl, isopropyl, t-butyl, methoxymethyl, benzyl and hexyl), substituted or unsubstituted alkenyl of 2 to 7 carbon atoms (such as a ethenyl, isopropenyl and allyl), or carbocyclic aryl of 6 to 10 carbon atoms in the ring system (such as phenyl, tolyl, xylyl, naphthyl and p-methoxyphenyl).

Alternatively, any two or three of $R^2$, $R^3$ and $R^4$ can be taken together to represent sufficient carbon atoms and an oxygen, nitrogen or sulfur atom to complete, with the quaternary ammonium atom, a 5- to 16-membered heterocyclyl cationic group. Examples of such groups include, but are not limited to pyridinium, piperidinium, pyrrolidinium, morpholinium, quinolinium, pyrimidinium, acridinium, benzothiazolium, benzoxazolinium and imidazolium.

Preferably, $R^2$, $R^3$ and $R^4$ are independently methyl or ethyl.

$X^-$ is a suitable monovalent acid anion which is not a substrate or inhibitor for peroxidases, including but not limited to, perchlorate, halide (such as fluoride, chloride and bromide), tetrafluoroborate, triflate, methyl sulfate, hexafluorophosphate, nitrate, p-toluenesulfonate and others readily apparent to one skilled in the art. Halide anions are preferred.

Examples of useful nonpolymeric cationic surfactants are hexadecyltrimethylammonium chloride, dodecyltrimethylammonium chloride, cetyltrimethylammonium bromide (also known as hexadecyltrimethylammonium bromide), cocotrimethylammonium chloride, tallowtrimethylammonium chloride, soyatrimethylammonium chloride, myristyltrimethylammonium bromide, stearyltrimethylammonium chloride, cetylethyldimethylammonium bromide, didodecyldimethylammonium bromide, cetylpyridinium chloride and myristyldimethylbenzylammonium chloride.

Cetyltrimethylammonium bromide is most preferred.

Many of these surfactants are readily available from a number of commercial sources. Others can be readily prepared by a skilled chemist using known starting materials and procedures.

Where $R^1$ in structure (I) is a polymeric moiety, the backbone of such polymers can be conventional polyesters, polyamides, polyethyleneimines, polycarbonates, cellulosic materials, and vinyl addition homo- and copolymers comprised of recurring units of a monomer having the desired positive charge. These materials can be prepared from conventional materials using conventional procedures. The polymer can have the charges incorporated therein from starting materials, or from chemical reaction after preparation.

Particularly useful cationic polymers are vinyl addition homo- or copolymers prepared from ethylenically unsaturated polymerizable monomers having the requisite positively charged groups, and one or more comonomers which provide hydrophobic regions characteristic of surfactants, crosslinked regions or other suitable properties.

Representative cationic monomers include, but are not limited to, N-cyclohexyl-N,N-dimethyl-N-(m- & p-vinylbenzyl)ammonium chloride, N-benzyl-N,N-dimethyl-N-(m- & p-vinylbenzyl)ammonium chloride, 3-(2-hydroxypropyl)-1-vinylimidazolium chloride and 1-methyl-4-vinylpyridinium chloride. Useful comonomers include, but are not limited to, styrene and its derivatives (such as vinyltoluene and p-t-butylstyrene), acrylic and methacrylic acid esters (such as methyl acrylate, methyl methacrylate, butyl acrylate and butyl methacrylate), crosslinkable monomers {such as divinylbenzene, ethylene diacrylate, ethylene dimethacrylate and N,N'-methylenebis(acrylamide)]. Other useful polymers are described, for example, as mordants in U.S. Pat. No. 4,069,017 (Wu et al) and U.S. Pat. No. 4,024,839 (Wu et al). Such materials generally have a quaternary ammonium or quaternary phosphonium groups pendant from the polymer backbone, and preferably at least from about 40 to 100 weight percent of the ethylenically unsaturated polymerizable monomer derived recurring units have such groups. The remaining recurring units can be derived from a wide variety of ethylenically unsaturated polymerizable monomers as noted in the patents identified above.

Representative cationic polymers include, but are not limited to, poly(N,N,N-trimethyl-N-vinylbenzylammonium chloride), poly[styrene-co-benzyl-N,N-dimethyl-N-(m- & p-vinylbenzyl)ammonium chloride-co-divinylbenzene], poly(N,N,N-trioctyl-N-vinylbenzylphosphonium chloride), poly[styrene-co-N-vinylbenzyl-N,N,N-trihexylammonium chloride], poly(styrene-co-N,N,N-trimethyl-N-vinylbenzylammonium chloride), poly[N-cyclohexyl-N,N-dimethyl-N-(m- & p-vinylbenzyl)ammonium chloride], poly[styrene-co-1-vinylimidazole-co-3-(2-hydroxyethyl)-1-vinylimidazolium chloride] and others readily apparent to one skilled in the art. A preferred cationic polymer is poly[N-cyclohexyl-N,N-dimethyl-N-(m- & p-vinylbenzyl)ammonium chloride].

The composition of this invention is generally buffered to a pH of from about 7 to about 9.5 using one or more suitable buffers well known in the art. For example, buffers such as tris(hydroxymethyl)aminomethane, borate, phosphate, bis-tris-propane and tricine can be used. Tris(hydroxymethyl)aminomethane is preferred.

In the composition of this invention, the amounts of each component can be varied depending upon where it is intended for use, the particular sensitivity of the reagents and other factors well understood by one skilled in the art. Thus, the following general ranges are meant to provide guidance for the skilled worker, and not to limit the practice of this invention.

The amount of buffer would be readily apparent to a skilled worker since it is well known how much of any buffer is needed to maintain a desired pH. The amount of DPD is generally at least about 0.01 mmolar, with an amount in the range of from about 0.1 to about 10 mmolar being preferred. The 4'-hydroxyacetanilide is generally present in an amount of at least about 0.01 mmolar, with an amount in the range of from about 0.05 to about 5 mmolar being preferred.

The nonpolymeric cationic surfactant is present in an amount which is from about 0.05 to about 0.25% above its critical micelle concentration. This can be readily determined for a given surfactant since the "critical micelle concentration" for many surfactants is well known, or can be readily determined using procedures described, for example, in *Surfactant Science and Technology*, Meyers, VCH Publishers, N.Y., Chapter 3, 1988. If a cationic polymer is included in the composition, it is present in an amount of from about 0.01 to about 2% (by weight).

Besides the stabilized aqueous composition described above, the present invention also provides a kit of individually packaged reagents, equipment and instructions useful for carrying out a variety of analytical methods (described below). The packaging of kit components is well known in the art.

In one embodiment, a kit comprises, individually packaged: a DPD as described above, and one or more of a cationic surfactant or cationic polymer as described above, 4'-hydroxyacetanilide and a peroxidase or peroxidase-labeled specific binding species. The kit preferably contains 4'-hydroxyacetanilide as one component besides the DPD. By "specific binding species" is meant any biological or chemical compound which will specifically bind with a receptor therefor which will not bind with other materials. Useful specific binding species include, but are not limited to, antibodies, non-immunoreactive proteins (such as avidin and some enzymes), antigens, haptens, vitamins such as biotin, lectins, sugars, peptides, polypeptides, oligonucleotides, nucleic acids and cell surface binding species. Particularly useful labeled specific binding species are peroxidase-labeled proteins or oligonucleotides. Such proteins include antibodies and avidin. Suitable receptors for given specific binding species are well known. Other components useful in an assay (such as an oxidant, described below) can be included in the test kit.

The present invention can be used in any method for the detection of a given analyte where the production of a chemiluminescent signal in response to the analyte is desired. In most instances, the signal is generated in response to the presence of peroxidase, which may be the analyte. Alternatively, peroxidase can be made available for reaction as a result of the presence of another analyte. Peroxidase, in the presence of the DPD, 4'-hydroxyacetanilide and an oxidant, will produce the emission of light which can be measured using suitable equipment.

By "peroxidase" is meant any peroxidative substance (enzymatic or otherwise) which catalyzes the oxidation of a DPD, such as luminol, to produce light. Microbial, fungal and plant peroxidases are preferred with horseradish peroxidase being most preferred. The amount of peroxidase can vary widely due to the amount of other components used in the reaction. A useful amount would be readily apparent to one skilled in the art, but a minimum amount would generally be at least about $1 \times 10^{-7}$ I.U./ml (or equivalent amount for nonenzymatic peroxidative substances). As used herein, I.U. represents the International Unit for enzyme activity and is defined as the amount of enzyme activity required to catalyze the conversion of 1 micromole of substrate to product per minute under standard pH and temperature conditions.

An oxidant is needed to cause excitation of the DPD so that light is emitted in the presence of peroxidase and 4'-hydroxyacetanilide. Various useful oxidants are known, but perborate ion and hydrogen peroxide are preferred with the latter being most preferred. The amount of oxidant used in a given assay is readily apparent to one skilled in the art, but a minimum amount of about 0.1 mmolar is generally used.

In some methods of this invention, peroxidase is used in "free form" (non-conjugated) for clinical analysis. In specific binding methods, however, the peroxidase is used as a conjugate with a specific binding ligand or receptor therefor, or with a specific binding molecule which is reactive with either the ligand or receptor. The ligand and receptor are complexed in such assays and thereby labeled with the peroxidase for eventual detection of the complex or uncomplexed materials. The preparation of such conjugates can be achieved using a variety of known techniques (for example, as described by Yoshitake et al, *Eur.J.Biochem.*, 101, 395, 1979, and in U.S. Pat. No. 5,106,732 of Kondo et al).

Various specific binding assay formats are useful in the practice of this invention, and include nucleic acid hybridization assays, immunochemical assays (such as enzyme immunoassays, sandwich assays, competitive binding assays, direct binding assays) and others well known in the art. Such assays are generally described, for example in U.S. Pat. No. 4,598,044, U.S. Pat. No. 4,745,077 (Holian et al), U.S. Pat. No. 5,077,198 (Shih et al), U.S. Pat. No. 5,085,986 (Mauck et al), Matthews et al, *Anal.Biochem.* 169, pages 1–25 (1988), and WO 88/01302 (published Feb. 25, 1988) The method of the invention can be preceeded by an amplification process, such as polymerase chain reaction (commonly known as PCR) as described for example in U.S. Pat. No. 4,965,188 (Mullis et al) and ligase chain reaction which is generally described by Weiss *Science*, 254, pages 1292–3, 1991 to increase the amount of targeted nucleic acid which can then be detected using the composition of this invention.

Thus, the method of this invention can be used to detect any of a wide variety of chemical and biological materials, such as amino acids, peptides, polypeptides, proteins (including enzymes, avidin, antibodies and antigenic proteins), carbohydrates (including monosaccharides, polysaccharides and lipopolysaccharides), hormones (such as human chorionic gonadotropin, thyroid stimulating hormone, leutinizing hormone, thyroxin, follicle stimulating hormone, parathyroid hormone and growth hormone), metabolites (such as glucose, lactate and pyruvate), oligonucleotides, nucleic acids, vitamins (such as $B_{12}$ and biotin), intact cells from various organisms (including microorganisms) and drugs (narcotics, therapeutic and those abused).

Particularly useful specific binding methods of this invention are those known in the art as sandwich assays whereby the ligand of interest is complexed with at least a first and second receptor either simultaneously or in a desired sequence. One of the receptors is insolubilized on a suitable support (such as microtiter plate, polymeric, magnetic or glass particles, film, membrane, filter paper and others known in the art) by adsorption, covalent or other known attachment procedures, or is capable of being insolubilized through further complexation or reaction. For example, the receptor can be labeled with a specific binding moiety (for example, biotin) which is reactive with its corresponding receptor moiety (for example, avidin) which is insolubilized on the support.

In the sandwich assays, the second receptor for the ligand of interest can be labeled with peroxidase, or is capable of being so labeled through additional specific binding reactions. Detection of the label is accomplished using the reagents described above.

In more preferred embodiments, the ligand of interest is an antigenic material with which antibodies are reactive, or a nucleic acid with which complementary nucleic acids (such as oligonucleotides) can be hybridized.

The assays described above can be carried out in solution or in a dry format. Solution assays generally refer to methods carried out in solution in a suitable container, and in the case of heterogeneous specific binding assays, suitable separation techniques and equipment are then used to separate unbound materials from the bound materials. In dry assays, chemical or specific binding reactions can be carried out in a dry element, test strip or fibrous sheet and the presence of the analyte is detected by adding the stabilized chemiluminescent composition of this invention. For example, a specific binding reaction can be carried out using a peroxidase-labeled specific binding material which is used to generate a chemiluminescent signal. Details regarding such elements are well known in the art, including for example, U.S. Pat. No. 4,670,381 (Frickey et al).

The following examples are provided to illustrate the practice of this invention, but are not intended to be limiting. All percentages are by weight, unless otherwise noted.

Except where noted, all reagents and equipment were obtained from Eastman Kodak Company or other commercial sources.

EXAMPLE 1

Solution assay for Peroxidase Comparing the Use of Cationic Surfactant with Different Enhancers A solution assay for peroxidase was carried out using an aqueous chemiluminescent composition of this invention containing 4'-hydroxyacetanilide as the enhancer, and comparing it to the use of a similar composition containing 4-iodophenol as the enhancer.

The following were mixed in a 1.5 ml polypropylene tube: horseradish peroxidase (24.3 pmolar, Sigma Chemical XII grade), luminol (1 mmolar), cetyltrimethylammonium bromide cationic surfactant (0.1% weight/volume), 4'-hydroxyacetanilide (0.333 mmolar) and tris(hydroxymethyl aminomethane, hydrochloride buffer (0.1 molar, pH 8) to form a stabilized composition of this invention (300 μliter total volume).

A similar composition Control A, 0.333 mmolar enhancer) was prepared without the cationic surfactant and placed in a separate tube.

Control B contained 4-iodophenol (0.444 mmolar) but no cationic surfactant, and was placed in a tube.

Control C contained 4-iodophenol (0.333 mmolar) and cationic surfact (0.1% weight/volume), and was placed in a tube.

Control D contained no enhancer and no cationic surfactant, while Control E contained the surfactant (0.1% weight/volume) but no enhancer.

After addition of hydrogen peroxide to each tube (2 mmolar) and vortex mixing, the chemiluminescent light signal in each tube was measured after 4.5 minutes using a conventional Turner luminometer (10 second integral light units) and standard procedures. The results are shown in the following Table I.

TABLE I

| Assay | Chemiluminescent Signal (Light Units) |
|---|---|
| Example 1 | 14.9 |
| Control A | 15.1 |
| Control B | 232.1 |
| Control C | 0.16 |
| Control D | 0.02 |
| Control E | 0.17 |

The data indicate that the presence of cationic surfactant did not adversely affect the signal when 4'-hydroxyacetanilide was used as the enhancer (Control A and Invention). However, when 4-iodophenol was used as an enhancer, the signal was greatly reduced by the presence of cationic surfactant (Control B vs. Control C). Controls D and E show the background signal of the composition with and without cationic surfactant. Example 1 is an improvement over Control A because the duration of the light signal was longer, as observed in separate, but similar tests where continuous rather than fixed-time measurements were made.

EXAMPLES 2–7

Comparative Use of Various Cationic Materials

In these examples, several different cationic surfactants and cationic polymers were evaluated for their effects on the chemiluminescent signal using 4'-hydroxyacetanilide as the enhancer. Assays for various amounts (see Table II) of horseradish peroxidase were carried out. Controls F-K were similarly carried out using 4-iodophenol as the enhancer. Controls L and M were carried out using 4'-hydroxyacetanilide and 4-iodophenol as the enhancer, respectively, but in the absence of a cationic surfactant or polymer.

To the test wells of a microtiter plate were added a composition (200 μl total volume) containing: horseradish peroxidase (various amounts), luminol (1 mmolar), hydrogen peroxide (2 mmolar, added last), cationic material (various amounts), diethylenetriaminepentaacetic acid (0.1 mmolar), tris(hydroxymethyl)aminomethane, hydrochloride (0.05 molar, pH 8) and enhancer (0.15 mmolar). Five minutes after addition of hydrogen peroxide to each test well, the chemiluminescent signals were measured for a 10 second interval using a conventional LabSystems Luminoskan ™ microplate reader.

The cationic materials and amounts used in each test are defined below, and Table II shows the data obtained as an average of three separate experiments.

Example 2: cetyltrimethylammonium bromide (0.1%),

Example 3: poly[N-cyclohexyl-N,N-dimethyl-N-(m- & p-vinylbenzyl)ammonium chloride](0.25%), Example 4: poly[styrene-co-N-benzyl,N,N-dimethyl-N-(m- & p-vinylbenzyl)ammonium chloride-co-divinylbenzene] (molar ratio 4.95:4.95:0.1) (0.05%), Example 5: poly[styrene-co-1-vinylimidazole-co-3-(2-hydroxyethyl)-1-vinylimidazolium chloride] (molar ratio 5:4:1) (0.025%), Example 6: poly[N-cyclohexyl-N,N-dimethyl-N-(m- & p-vinylbenzyl)ammonium chloride](0.25%), and Example 7: poly[styrene-co-1-vinylimidazole-co-3-(2-hydroxyethyl)-1-vinylimidazolium chloride] (molar ratio 4.4:2:3.6) (0.1%).

TABLE II

| Amount of Peroxidase (p-molar) | Chemiluminescent Signal (Light Units) | | | | | | | | | | | |
|---|---|---|---|---|---|---|---|---|---|---|---|---|
| | Control L | Example 2 | (S/N)* | Example 3 | (S/N) | Example 4 | (S/N) | Example 5 | (S/N) | Example 6 | (S/N) | Example 7 | (S/N) |
| 0 | 0.00 | 0.3 | | 0.10 | | 0.05 | | 0.10 | | 0.14 | | 0.04 | |
| 0.25 | 0.14 | 0.42 | 14 | 0.29 | 2.9 | 0.18 | 3.6 | 0.25 | 2.5 | 0.34 | 2.4 | 0.22 | 5.5 |
| 2.5 | 1.88 | 6.19 | | 3.17 | | 2.22 | | 2.08 | | 3.96 | | 2.87 | |
| 25 | 13.19 | 53.89 | | 28.30 | | 14.32 | | 16.51 | | 38.47 | | 26.17 | |
| 250 | 80.84 | 321 | | 201.33 | | 173.33 | | 100.19 | | 360.00 | | 200.61 | |

| Amount of Peroxidase (p-molar) | Chemiluminescent Signal (Light Units) | | | | | | | | | | | |
|---|---|---|---|---|---|---|---|---|---|---|---|---|
| | Control M | Control F | (S/N) | Control G | (S/N) | Control H | (S/N) | Control I | (S/N) | Control J | (S/N) | Control K | (S/N) |
| 0.0 | 0.00 | 0.07 | | 0.10 | | 0.05 | | 0.10 | | 0.16 | | 0.08 | |
| 0.25 | 0.03 | 0.09 | 1.28 | 0.08 | 0.8 | 0.06 | 1.2 | 0.11 | 1.1 | 0.20 | 1.2 | 0.07 | 0.88 |
| 2.5 | 2.19 | 0.24 | | 2.53 | | 0.57 | | 1.86 | | 0.76 | | 0.63 | |
| 25 | 52.89 | 6.56 | | 59.21 | | 18.44 | | 41.74 | | 28.22 | | 33.09 | |

TABLE II-continued

| 250 | 805.67 | 146.00 | 883.00 | 416.00 | 726.33 | 727.00 | 719.67 |

S/N = signal to noise ratio (noise being at 0 pmolar peroxidase)

These data indicate that all of the cationic materials increased the chemiluminescent signal at all enzyme levels when 4'-hydroxyacetanilide was used as an enhancer. This effect is further evidenced by the signal to noise ratio being greater than about 2 for those assays carried out at 0.25 pmolar horseradish peroxidase. The S/N ratio at that concentration was at or below about 1.3 when 4-iodophenol was used as an enhancer, thus showing that the apparent rise in signal over Control M was due to a blank increase alone. At other levels of enzyme concentration, using 4-iodophenol, the cationic materials either caused a decrease in signal or had no effect.

EXAMPLE 8

Comparisons with Nonionic and Anionic Surfactants

This example demonstrates that the presence of a cationic surfactant stabilizes the chemiluminescent composition, but nonionic and anionic surfactants do not achieve the same result.

The compositions used were like those shown for Examples 2-7 above. Controls N and N' contained no surfactant. Example 8 and Controls O-T were carried out using 4'-hydroxyacetanilide as the enhancer. Controls S-W were carried out using 4-iodophenol as the enhancer. The following surfactants were used (each at 0.1%):

Example 8 and Control S: cetyltrimethyl-ammonium bromide,

Controls 0 and T: TRITON TM X-100 octylphenoxy polyethoxy ethanol nonionic surfactant (Rohm and Haas), Controls P and U: BRIJ TM 35 polyoxyethylene lauryl ether nonionic surfactant (Honeywell-Atlas Ltd.), Controls Q and V: TWEEN TM 20 polyoxyethylene sorbitan monolaurate nonionic surfactant (ICI Americas, Inc.), and Controls R and W: sodium dodecyl sulfate anionic surfactant.

The chemiluminescent assays were carried out as described in Examples 2-7 at various concentrations of horseradish peroxidase. The results are presented in Table III below.

creased with the nonionic and anionic surfactants in the presence of both enhancers.

EXAMPLE 9

Solution Assay for Thyroid Stimulating Hormone

This example demonstrates the practice of this invention for the determination of thyroid stimulating hormone (TSH) in a solution, and compares it to assays outside the scope of this invention.

The invention was carried out similar to the commercially available AMERLITE TM TSH assay using the same equipment and reagents, except as noted below TSH calibrator solutions were used as test specimens.

The chemiluminescent signal generating compositions used were as follows:

Control X: Contained luminol (0.125 mmolar), 4-iodophenol (0.1 mmolar), perborate (1 mmolar), benzoate (0.56 mmolar) and citrate (3.5 mmolar) in borate buffer (0.1 molar, pH 8.5).

Control Y: Contained Control X and in addition, cetyltrimethylammonium bromide (0.1%).

Example 9: 4'-hydroxyacetanilide (0.15 mmolar), luminol (1 mmolar), hydrogen peroxide (2 mmolar), diethylenetriaminepentaacetic acid (0.1 mmolar), cetyltrimethylammonium bromide (0.1%) and tris(hydroxymethyl)aminomethane, hydrochloride (0.05 molar, pH 8).

Control Z: Same as Example 9 except 4-iodophenol (0.15 mmolar) was used in place of 4'-hydroxyacetanilide.

The AMERLITE TM TSH assay protocol was then followed using commercially available microtiter plates having anti-TSH monoclonal antibody adsorbed on the walls of the test wells. Generally, this protocol included:

a) Adding assay reagent (100 μl) containing a bacteriostat to the test wells.

b) Adding the test specimen (100 μl) to the test wells.

c) Incubating the plates at 37° C. for 30 minutes in the AMERLITE TM Shaker Incubator.

d) Aspirating fluid from and washing all test wells with the AMERLITE TM Washer.

e) Adding anti-TSH-horseradish peroxidase mono-

TABLE III

| Amount of Peroxidase (pmolar) | Chemiluminescent Signal (Light Units) | | | | | | | |
|---|---|---|---|---|---|---|---|---|
| | Control N | Example 8 | Control O | Control P | Control Q | Control R | Control N' | Example S |
| 0 | 0.00 | 0.02 | 0.00 | 0.00 | 0.00 | 0.00 | 0.00 | 0.06 |
| 0.25 | 0.10 | 0.24 | 0.06 | 0.07 | 0.08 | 0.09 | 0.01 | 0.07 |
| 2.5 | 1.72 | 4.12 | 1.23 | 1.21 | 1.28 | 1.40 | 0.84 | 0.17 |
| 25 | 14.26 | 33.84 | 9.25 | 8.79 | 9.08 | 10.46 | 30.69 | 3.71 |
| 250 | 99.61 | 232.67 | 59.31 | 57.18 | 56.46 | 67.71 | 773.33 | 93.29 |

| Amount of Peroxidase (pmolar) | Chemiluminescent Signal (Light Units) | | | |
|---|---|---|---|---|
| | Control T | Control U | Control V | Control W |
| 0 | 0.00 | 0.00 | 0.01 | 0.00 |
| 0.25 | 0.00 | 0.00 | 0.00 | 0.00 |
| 2.5 | 0.21 | 0.50 | 0.60 | 0.58 |
| 25 | 11.81 | 18.39 | 18.29 | 20.48 |
| 250 | 291.67 | 376.33 | 319.67 | 491.33 |

These data indicate that only the cationic surfactant, in the presence of 4'-hydroxyacetanilide (Example 8), increases the chemiluminescent signal. Signals are declonal antibody conjugate (200 μl) to the test wells, and incubating at 37° C. for about 30 minutes while being shaken.

f) Aspirating fluid from and washing all test wells.

g) Adding the signal generating reagent to each test well.

h) Within 5 minutes, measuring the chemiluminescent signal (in light units) produced as described in Examples 2-7.

The results of these assays are provided in Table IV below (as the average of two tests).

TABLE IV

| Amount of TSH | Chemiluminescent Signal | | | | | | | |
|---|---|---|---|---|---|---|---|---|
| (μI.U./ml) | Control X | (S/N)* | Control Y | (S/N) | Example 9 | (S/N) | Control Z | (S/N) |
| 0 | 6.32 | | 32.36 | | 5.08 | | 7.37 | |
| 0.22 | 11.22 | 1.78 | 38.18 | 1.18 | 31.31 | 6.16 | 8.61 | 1.17 |
| 1.00 | 303.11 | 48 | 40.56 | 1.25 | 182.82 | 36 | 43.12 | 5.8 |
| 4.91 | 2975.32 | 471 | 190.98 | 5.9 | 1267.49 | 249 | 851.85 | 115.6 |
| 42.3 | 23455.17 | 3711 | 3422.84 | 106 | 7723.45 | 1520 | 8685.62 | 1178 |
| 196 | 76598.69 | 12120 | 14711.93 | 455 | 17887.63 | 3521 | 28061.77 | 3807 |

S/N = Signal to noise ratio as described above.

The data show that the use of a cationic surfactant with 4-iodophenol in Controls Y and Z decreases chemiluminescent signal and the signal to noise (S/N) ratio. The present invention whereby the cationic surfactant was used with 4'-hydroxyacetanilide provided improved sensitivity at lower concentrations of TSH analyte (e.g. 0.22 μI.U./ml). It is highly desired to detect TSH at the lowest possible concentration in order to distinguish hyperthyroid condition from euthyroid (normal) status. A S/N ratio greater than 2 is acceptable.

EXAMPLE 10

Assay Carried Out in Dry Analytical Element

This example demonstrates the practice of this invention for the determination of an analyte, horseradish peroxidase, in a dry analytical element. The element had the following structure and components:

| | Dry Coverage g/m² |
|---|---|
| Spreading Layer | |
| Particles (30 μm) of Poly(vinyltoluene-co-methacrylic acid) (98.2 weight ratio) | 130 |
| Poly(methyl acrylate-co-sodium 2-acrylamido-2-methylpropanesulfonate-co-2-acetoacetoxyethyl methacrylate) (90:4:6 molar ratio) | 2.583 |
| Tris(hydroxymethyl)aminomethane buffer (pH 8) | 1.21 |
| Diethylenetriaminepentaacetic acid | 0.0039 |
| ZONYL ™ FSN nonionic surfactant | 0.054 |

| | Dry Coverage g/m² |
|---|---|
| pH adjusted to 8 with HCl before coating | |
| Reagent Layer | |
| Hardened gelatin | 10.15 |
| Tris(hydroxymethyl)aminomethane buffer (pH 8) | 1.21 |
| Diethylenetriaminepentaacetic acid | 0.004 |
| TRITON ™ X-100 nonionic surfactant | 0.02% of total |
| pH adjusted to 8 with HCl before coating | |
| Subbing Layer | |
| Poly(methyl acrylate-co-vinylidene chloride-co-itaconic acid) | |
| Poly(ethylene terephthalate) Support | |

A chemiluminescent signal generating composition was prepared using the following reagents:

luminol (1 mmolar),
hydrogen peroxide (2 mmolar),
diethylenetriaminepentaacetic acid (0.1 mmolar),
tris(hydroxymethyl)aminomethane, hydrochloride (0.05 molar, pH 8)
cetyltrimethylammonium bromide (0.1%),
4'-hydroxyacetanilide (0.15 mmolar, Example 10) or 4-iodophenol (0.4 mmolar, Control AA), and
horseradish peroxidase (amounts in Table V).

Control BB was similarly prepared with 4-iodophenol but the cationic surfactant was omitted, and Control CC was similarly prepared with 4'-hydroxyacetanilide but the cationic surfactant was omitted.

After addition of the peroxidase to the compositions and vortex mixing, a sample (10 μl) of each was applied to the spreading layer of individual elements (16 mm² surface area). After five minutes, the resulting chemiluminescent signals generated by the reagents in the element were measured using a 10 second integration of emitted light on a commercial Turner luminometer at 37° C. The results provided below in Table V are the average of two tests for each composition.

TABLE V

| Amount of | Chemiluminescent Signal (Light Units) | | | | | | | |
|---|---|---|---|---|---|---|---|---|
| Peroxidase (pmolar) | Example 10 | (S/N) | Control AA | (S/N) | Control BB | (S/N) | Control CC | (S/N) |
| 0 | 0.77 | | 1.14 | | 1.50 | | 1.07 | |
| 1 | 0.78 | 1.01 | 1.15 | 1.01 | 1.55 | 1.03 | 1.13 | 1.06 |
| 5 | 0.85 | 1.10 | 1.16 | 1.02 | 1.48 | 0.99 | 1.15 | 1.07 |
| 10 | 0.99 | 1.28 | 1.23 | 1.08 | 1.50 | 1.00 | 1.25 | 1.17 |
| 50 | 18.39 | 23.9 | 1.33 | 1.17 | 1.60 | 1.06 | 8.54 | 7.98 |
| 100 | 80.19 | 104.1 | 1.51 | 1.33 | 1.72 | 1.15 | 54.5 | 50.91 |
| 500 | 709.1 | 920.3 | 4.32 | 3.80 | 5.74 | 3.82 | 712.5 | 665.6 |
| 1000 | 1179.0 | 1530 | 349.35 | 307.2 | 613.7 | 408.6 | 931.1 | 869.7 |

The data show that the addition of the cationic surfactant to the composition increased the chemiluminescent signal and signal/noise (S/N) ratio at lower concentrations of analyte (e.g. 50 pmolar). The addition of the cationic surfactant to the composition containing 4-iodophenol actually reduced the signal at most analyte concentrations.

The presence of very low amounts of nonionic surfactants ZONYL™ FSN and TRITON™ X-100 used as coating aids in the coating formulations used to prepare the analytical element did not adversely affect the generation of a chemiluminescent signal in the assay.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

I claim:

1. An aqueous composition for providing a chemiluminescent signal having a pH of from about 7 to about 9.5 and comprising:
   a) a 2,3-dihydro-1,4-phthalazinedione derivative,
   b) a low molecular weight nonpolymeric weight cationic surfactant present at from about 0.05 to about 0.25 percent by weight above its critical micelle concentration, or from about 0.01 to about 2 percent by weight of a cationic polymer, and
   c) 4'-hydroxyacetanilide.

2. The composition of claim 1 wherein said cationic surfactant or cationic polymer is represented by the structure (I):

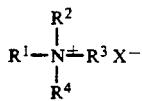

wherein $R^1$ is alkyl, aryl, alkenyl or a polymeric moiety, $R^2$ is alkyl, alkenyl or aryl, $R^3$ and $R^4$ are independently alkyl, alkenyl or aryl, and $X^-$ is an anion, or
   any two or three of $R^2$, $R^3$ and $R^4$ can be taken together to represent sufficient carbon atoms and an oxygen, nitrogen or sulfur atom, when taken with the quaternary ammonium atom, to complete a 5- to 16-membered heterocyclic group.

3. The composition of claim 2 wherein $R^1$ is alkyl or alkenyl of 14 to 16 carbon atoms, $R^2$, $R^3$ and $R^4$ are independently methyl or ethyl, and $X^-$ is halide.

4. The composition of claim 2 wherein said surfactant is cetyltrimethylammonium bromide.

5. The composition of claim 1 wherein said 2,3-dihydro-1,4-phthalazinedione derivative is represented by the structure (II):

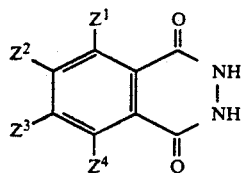

wherein
$Z^1$, $Z^2$, $Z^3$ and $Z^4$ are independently hydrogen, alkyl, alkenyl, hydroxy, alkoxy, carboxy, amino, conjugated aminoalkenyl or aminoaryl, provided that one of $Z^1$ and $Z^2$ is amino, conjugated aminoalkenyl or aminoaryl, or
   any adjacent two, adjacent three or all four of $Z^1$, $Z^2$, $Z^3$ and $Z^4$, when taken together, form a fused ring system.

6. The composition of claim 5 wherein said 2,3-dihydro-1,4-phthalazinedione derivative is luminol or isoluminol.

7. The composition of claim 1 wherein said 2,3-dihydro-1,4-phthalazinedione derivative is present in an amount of from about 0.1 to about 10 mmolar, and 4'-hydroxyacetanilide is present in an amount of from about 0.05 to about 5 mmolar.

8. A diagnostic test kit comprising individually packaged:
   a) a 2,3-dihydro-1,4-phthalazinedione derivative,
   b) a low molecular weight cationic surfactant present at from about 0.05 to about 0.25% above its critical micelle concentration, or from about 0.01 to about 2% of a cationic polymer,
   c) 4'-hydroxyacetanilide, and
   d) a peroxidase or peroxidase-labeled specific binding species.

9. The kit of claim 8 wherein said peroxidase-labeled specific binding species is a peroxidase-labeled protein or oligonucleotide.

10. The kit of claim 9 wherein said peroxidase-labeled protein is an antibody or avidin.

11. The kit of claim 8 further comprising an oxidant.

12. A method for producing a chemiluminescent signal in response to a peroxidase comprising
   A. reacting a peroxidase in the presence of:
      a 2,3-dihydro-1,4-phthalazinedione derivative,
      an oxidant,
      a low molecular weight nonpolymeric cationic surfactant present at from about 0.05 to about 0.25 percent by weight above its critical micelle concentration, or from about 0.01 to about 2 percent by weight of a cationic polymer, and
      4'-hydroxyacetanilide to produce a chemiluminescent signal, and
   B. determining the resulting signal as a measure of peroxidase.

13. The method of claim 12 wherein said cationic surfactant or cationic polymer is represented by the structure (I):

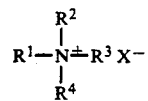

wherein $R^1$ is alkyl, aryl, alkenyl or a polymeric moiety, $R^2$ is alkyl, alkenyl or aryl, $R^3$ and $R^4$ are independently alkyl, alkenyl or aryl, and $X^-$ is an anion, or
   any two or three of $R^2$, $R^3$ and $R^4$ can be taken together to represent sufficient carbon atoms and an oxygen, nitrogen or sulfur atom, when taken with the quaternary ammonium atom, to complete a 5- to 16-membered heterocyclic group, and
   said 2,3-dihydro-1,4-phthalazinedione derivative is represented by the structure (II):

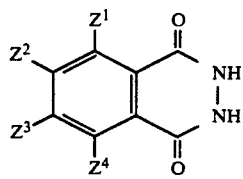

wherein

Z¹, Z², Z³ and Z⁴ are independently hydrogen, alkyl, alkenyl, hydroxy, alkoxy, carboxy, amino, conjugated aminoalkenyl or aminoaryl, provided that one of Z¹ and Z² is amino, conjugated aminoalkenyl or aminoaryl, or any adjacent two, adjacent three or all four of Z¹, Z², Z³ and Z⁴ when taken together, form a fused ring system.

14. The method of claim 12 wherein said peroxidase is present as an analyte or is present in free form for the detection of a non-immunological analyte other than peroxidase.

15. The method of claim 12 wherein said low molecular weight surfactant is hexadecyltrimethylammonium chloride, dodecyltrimethylammonium chloride, cetyltrimethylammonium bromide, cocotrimethylammonium chloride, tallowtrimethylammoniun chloride or soyatrimethylammonium chloride, myristyltrimethylammonium bromide, stearyltrimethylammonium chloride, cetylethyldimethylammonium bromide, didodecyldimethylammonium bromide, cetylpyridinium chloride or myristyldimethylbenzylammonium chloride, said 2,3-dihydro-1,4-phthalazinedione derivative is luminol, isoluminol, N-(4-aminobutyl)-N-ethylisoluminol hemisuccinimide, N-(6-aminohexyl)-N-ethylisoluminol, N-ethylisoluminol or 7-dimethylaminonaphthalene-1,2-dicarboxylic acid hydrizide, and said oxidant is hydrogen peroxide.

16. A specific binding assay for the determination of a specific binding ligand comprising:

A. complexing a specific binding ligand with a receptor specific for said ligand to form a specific binding complex, B. labeling said specific binding complex with a peroxidase which is either conjugated with said receptor, or is conjugated with a specific binding molecule which is specifically reactive with either said specific binding ligand or said receptor, C. separating uncomplexed materials from the resulting peroxidase-labeled complex, D. contacting said peroxidase-labeled complex with:
a 2,3-dihydro-1,4-phthalazinedione derivative,
an oxidant,
a low molecular weight nonpolymeric cationic surfactant present at from about 0.05 to about 0.25 percent by weight above its critical micelle concentration, or from about 0.01 to about 2 percent by weight of a cationic polymer, and
4'-hydroxyacetanilide to produce a chemiluminescent signal, and E. determining the resulting signal as a measure of said specific binding ligand.

17. The method of claim 16 wherein said surfactant is a cationic surfactant represented by the structure (I):

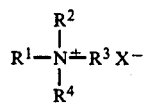

wherein R¹ is alkyl, aryl, alkenyl or a polymeric moiety, R² is alkyl, alkenyl or aryl, R³ and R⁴ are independently alkyl, alkenyl or aryl, and X⁻ is an anion, or any two or three of R², R³ and R⁴ can be taken together to represent sufficient carbon atoms and an oxygen, nitrogen or sulfur atom, when taken with the quaternary ammonium atom, to complete a 5- to 16-membered heterocyclic group, said 2,3-dihydro-1,4-phthalazinedione derivative is represented by the structure (II):

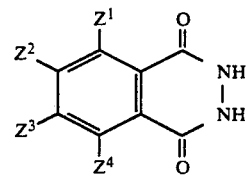

wherein

Z¹, Z², Z³ and Z⁴ are independently hydrogen, alkyl, alkenyl, hydroxy, alkoxy, carboxy, amino, conjugated aminoalkenyl or aminoaryl, provided that one of Z¹ and Z² is amino, conjugated aminoalkenyl or aminoaryl, or any adjacent two, adjacent three or all four of Z¹, Z², Z³ and Z⁴ when taken together, form a fused ring system, and said oxidant is hydrogen peroxide.

18. The method of claim 16 wherein said 4'-hydroxyacetanilide is used in an amount of from about 0.05 to about 5 mmolar, and said 2,3-dihydro-1,4-phthalazinedione is used in an amount of from about 0.1 to about 10 mmolar.

19. The method of claim 16 wherein said 2,3-dihydro-1,4-phthalazinedione derivative is luminol or isoluminol, said surfactant is cetyltrimethylammonium bromide, and said oxidant is hydrogen peroxide.

20. The method of claim 16 wherein said specific binding ligand is complexed with a first and second receptor therefor, said first receptor being immobilized or capable of being immobilized through further complexation or reaction with a specific binding moiety and said second receptor being labeled with peroxidase or capable of being labeled with peroxidase, thereby forming a sandwich of said ligand and said first and second receptors.

21. The method of claim 20 for the determination of an antigen wherein said first and second receptors are antibodies specific to said antigen.

22. The method of claim 20 for the determination of a target nucleic acid wherein said first and second receptors are oligonucleotides which are complementary to sequences in different regions of said target nucleic acid.

23. The method of claim 16 for the determination of a target nucleic acid which has been amplified by subjection to an amplification reaction.

* * * * *

UNITED STATES PATENT AND TRADEMARK OFFICE
CERTIFICATE OF CORRECTION

PATENT NO. : 5,279,940

DATED : January 18, 1994

INVENTOR(S) : Thomas R. Kissel

It is certified that error appears in the above-identified patent and that said Letters Patent is hereby corrected as shown below:

Column 17, line 26, reading "b) a low molecular weight nonpolymeric weight" should read --b) a low molecular weight nonpolymeric--.

Signed and Sealed this

Thirty-first Day of May, 1994

*Attest:*

*Attesting Officer*

BRUCE LEHMAN

*Commissioner of Patents and Trademarks*